Oct. 29, 1935. M. C. AMLING Plant Pat. 144
HYBRID TEA ROSE
Filed March 2, 1935
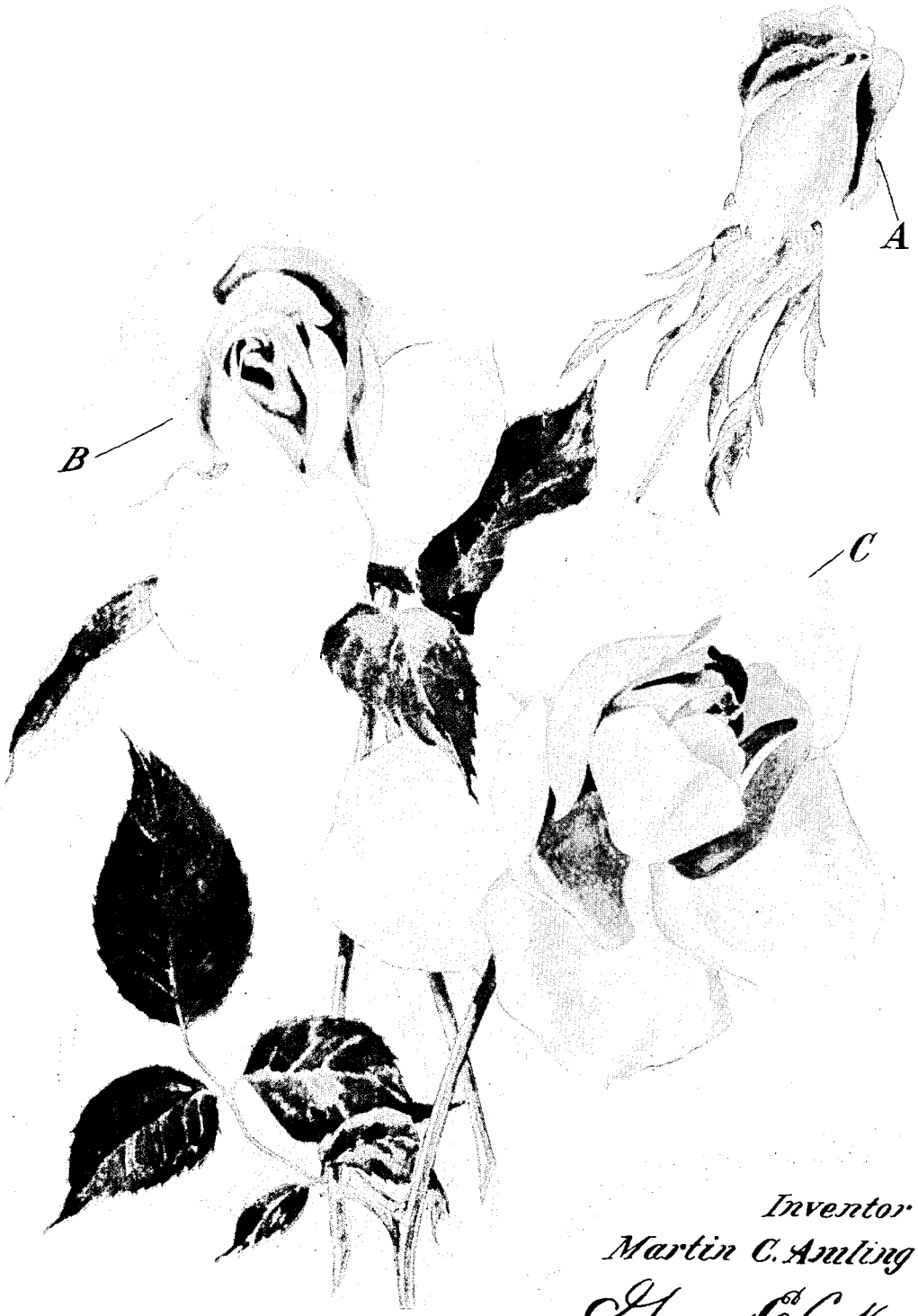
Inventor
Martin C. Amling
George E. Cook,
Attorney

UNITED STATES PATENT OFFICE

144

HYBRID TEA ROSE

Martin C. Amling, Pana, Ill., assignor to Amling Rose Company, Pana, Ill., a corporation of Illinois Application March 2, 1935, Serial No. 9,084

1 Claim. (Cl. 47—61)

My invention relates to improvements in fragrant hybrid tea roses. The object of my invention is to provide a new and distinct variety of rose of the type mentioned, which is unique in character, or unusual beauty in appearance, and of prolific bloom.

My present invention comprises a new and distinct variety of rose, the same being first naturally produced as a sport from a rose commonly known as Briarcliff, then developed through successive vegetation propagations, whereby its characteristics have become fixed and its identity preserved and from which it will not retrogress to its progenitor by protracted asexual propagation, or otherwise. These characteristics of color, appearance and stability have been proven to persist by repeated grafting and budding of said rose since the year 1932.

My new rose was produced as follows: A Briarcliff rose plant, which normally produces blooms light pink in color, produced a sport having a color range from Tyrian rose and rose color to deep rose pink and amaranth pink. (These color readings from Ridgway's Color Standards, Plate XII.) Buds from the branch which bore the sport bloom were budded and re-budded for a number of times and came true to the original sport bloom, whereby the color and other characteristics (as enumerated herein) of the original sport were recognized as being fixed; scions of the original sport plant have been grafted to Dutch and English Manetti, and each time they were grafted to this Manetti the plant came true to the original sport in bloom, color and other characteristics; and my new rose may now be reproduced by grafting or budding or otherwise, without deterioration in color or change in characteristics.

Other objects and characteristics of my new rose will be more fully specified in the following description, and the essential characters will be pointed out in the appended claim.

The accompanying illustration, forming a part of this specification, shows my new rose in its natural colors, wherein letter A denotes a bud beginning to open; letter B denotes a partially developed bud; and letter C denotes a full blown rose.

My new rose is similar to the Briarcliff rose of which it is a sport, except as to the color of the bloom, wherein the Briarcliff rose is a light pink and my rose has a color range from Tyrian rose and rose color to deep rose pink and amaranth pink; also this rose has fewer small petals and more large petals, which larger petals are usually from 40 to 52 in number to each bloom in the month of February in the latitude of Chicago. It also differs in that it is more fragrant than its progenitor; and the fragrance remains with the bloom for many hours after its being cut from the plant. The plant is unusually free flowering and the blooms are of very large size. They also have a decided brillance of color. Referring to Ridgway's Color Standards and Nomenclature, I describe my rose as follows:

General effect
- Interior of bloom, rose color.....Plate XII

Outside petals
- Outside white edged mallow pink.....Plate XII
- Inside light mallow purple.....Plate XII Intermediate petals
- Outside, edge rose color, center rose pink.....Plate XII
- Inside, between rhodamine purple and rose color, with a white base.....Plate XII Inside petals
- Outside, edge of Tyrian pink.....Plate XII
- Inside, between Tyrian rose and rhodamine purple.....Plate XII Number of petals 33.

The color is rather uniformly dispersed over the petal surfaces, but of course shows different shades in different lights. This new variety is of a deeper and more pronuonced color than the variety "Briarcliff Brilliance" which is also a sport of Briarcliff. The buds are more pointed and the edges of the petals show less disposition to curl than in the case of Briarcliff Brilliance. The stipules are less foliaceous in character and the points less given to long curled extensions than in the case of Briarcliff Brilliance.

This new rose also differs from the Briarcliff rose in that it has unusually straight, practically unthorned, stems; and in that the neck or stem of the rose immediately adjoining the bloom is of exceedingly strong texture so that for many hours after the rose has been cut from the plant the bloom will not wither in water nor will the bloom of the rose droop or have a tendency to hang down, and the stem remains rigid, permitting the bloom to fully open when placed in a container of water.

An additional feature of my rose is that during the winter season when it is grown in greenhouses under artificial conditions, the color of the bloom of this rose will not and does not materially fade but the bloom of the rose remains much the same color when grown artificially as when grown out of doors, regardless of the season of the year.

An additional feature of my rose is that it will produce blooms almost as prolifically in the winter season as it does in the summer season; and that this rose does not become dormant in the winter season and is a free grower when grown in greenhouses in the dark winter months.

Additional characteristics of my new plant are as follows:

*Foliage.*—Uniformly appearing upon the bush at intervals from 2½ to 3 inches apart. Stipules, narrow, long, highly developed and very uniform. On the first leaf branch below the blossom, they do not curl or circle or have a tendency to droop but afford almost a perfect union with the petiole or leaf-stalk. The leaves have uniform toothed edges and the leaves appearing upon the stem below the first leaf joined below the blossom, are almost uniform and each rachis contains from five to seven leaves, the color of the upper surface being Cossack green, Plate VI, and the under surface Rivage green, Plate XVIII. The top side of said leaves is very radiant and of a waxy surface.

*Hips.*—Moderately tapered.

*Buds.*—Immediately before opening the buds have an average length of 1½ inches and before opening they have a tendency toward regularity of form, which tendency of regularity continues until the full development of the flower.

*Sepals.*—The calyx is made up of five sepals which extend from 1½ to 2 inches beyond the ovary. At the base of from one to three of the sepals are small leaflike appendages closely resembling a stipule. The sepals hold their horizontal position and do not curl from the calyx when cut and kept in water for three or four days.

*Blossoms.*—Double. In the cutting stage measure about 1½ inches across the top and open out later to approximately 3½ to 4 inch spread.

*Petals.*—Regularly arranged from the outer petals to the stamens, which form the center of the rose. Uniformly obovate in shape, soft, inside velvety, outside satiny. They number from 40 to 52 in a full open rose during the months of December and January and maintain the quality and quantity during the entire year.

*Bush.*—Is an upright, free grower and requires very little pinching. The stalks or stems are straight and average from 18 to 21 inches in length without pinching. The thorns run and appear uniform completely from the top to the bottom of the plant. Responds rapidly in growth to fertilization when applied in the usual and customary greenhouse treatment.

I desire that it be understood that variation is to be allowed in the description of my rose, because the size of the bloom, the brightness or brilliancy, the paleness, and the color shade thereof will vary somewhat on account of differences in soil, the amount of sunshine and moisture, and the plant's freedom from disease, fungus and insects; but such variations are but climatic or conditional and it is a well known fact that these conditions will affect all roses to various degrees.

Having now fully shown and described my new rose, together with its origin and the manner of its asexual production, what I claim and desire to secure by Letters Patent of the United States, is:

The variety of rose substantially as shown and described, characterized particularly by having a color range from Tyrian rose and rose color to deep rose pink and amaranth pink, a delicate and attractive fragrance of long duration, the bush unusually prolific of bloom and the bloom having very large-sized petals.

MARTIN C. AMLING.